(12) United States Patent
Nariyama

(10) Patent No.: US 10,797,337 B2
(45) Date of Patent: Oct. 6, 2020

(54) FLOW BATTERY

(71) Applicant: Panasonic Intellectual Property Management Co., Ltd., Osaka (JP)

(72) Inventor: Honami Nariyama, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 215 days.

(21) Appl. No.: 15/730,669

(22) Filed: Oct. 11, 2017

(65) Prior Publication Data

US 2018/0175427 A1 Jun. 21, 2018

(30) Foreign Application Priority Data

Dec. 15, 2016 (JP) ................. 2016-242810

(51) Int. Cl.
*H01M 2/38* (2006.01)
*H01M 8/18* (2006.01)
*H01M 8/00* (2016.01)
*H01M 8/22* (2006.01)
*C07D 209/88* (2006.01)

(52) U.S. Cl.
CPC .......... *H01M 8/188* (2013.01); *H01M 8/002* (2013.01); *H01M 8/225* (2013.01); *C07D 209/88* (2013.01); *H01M 2300/0025* (2013.01); *Y02E 60/528* (2013.01)

(58) Field of Classification Search
CPC ...... H01M 8/002; H01M 8/188; H01M 8/225; H01M 2300/0025; C07D 209/88; Y02E 60/528
See application file for complete search history.

(56) References Cited

U.S. PATENT DOCUMENTS

| | | | | |
|---|---|---|---|---|
| 2014/0134465 A1* | 5/2014 | Kumamoto | ........... | H01M 8/188 429/61 |
| 2014/0178735 A1* | 6/2014 | Wang | ...................... | H01M 8/20 429/105 |
| 2014/0203654 A1* | 7/2014 | Takahashi | ................. | H02J 1/00 307/82 |
| 2014/0370404 A1* | 12/2014 | Kato | ................... | H01M 8/0241 429/418 |

(Continued)

FOREIGN PATENT DOCUMENTS

JP 2014-524124 9/2014

OTHER PUBLICATIONS

Shirota et al., "Electrochemically Doped Poly(N-Vinylcarbazole) as an Electrode Material for Rechargeable Batteries", Synthetic Metals, vol. 41-14, pp. 1169-1172 (1991). (Year: 1991).*

(Continued)

*Primary Examiner* — Raymond Alejandro
(74) *Attorney, Agent, or Firm* — McDermott Will & Emery LLP

(57) ABSTRACT

A flow battery includes a first liquid containing a first electrode mediator dissolved therein, a first electrode immersed in the first liquid, a first active material immersed in the first liquid, and a first circulation mechanism that circulates the first liquid between the first electrode and the first active material, wherein the first electrode mediator includes a bicarbazyl derivative. For example, the bicarbazyl derivative is represented by the general formula (1).

19 Claims, 8 Drawing Sheets

(56) References Cited

U.S. PATENT DOCUMENTS

2014/0371421 A1* 12/2014 Shibano .............. C08G 61/124
528/423
2015/0280259 A1* 10/2015 Anderson ............. H01M 8/188
429/409

OTHER PUBLICATIONS

Lee et al., "Synthesis and Hole-Transporting Properties of Various Bicabazyl Derivatives", Journal of Nanoscience and Nanotechnology, vol. 8, pp. 4797-4802 (2008). (Year: 2008).*

* cited by examiner

FIG. 2

| COMPOUND NAME | STRUCTURAL FORMULA | ELECTRIC POTENTIAL: E1 (V vs. Li/Li+) | ELECTRIC POTENTIAL: E2 (V vs. Li/Li+) |
|---|---|---|---|
| 9,9'-DIPHENYL-9H,9H'-3,3'-BICARBAZYL | | 3.90 | 4.09 |
| 9,9'-BIS(p-TOLYL)-9H,9H'-3,3'-BICARBAZYL | | 3.85 | 4.08 |
| 9,9'-DIETHYL-9H,9H'-3,3'-BICARBAZYL | | 3.76 | 4.03 |

FIG. 5
| COMPOUND | MOLAR CONCENTRATION (M) | ELECTRIC POTENTIAL (V vs. Li/Li$^+$) |
|---|---|---|
| PHENANTHRENE 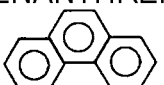 | 1 | 0.03 |
| BIPHENYL 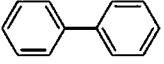 | 1 | 0 |
| O-TERPHENYL 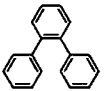 | 1 | 0.15 |
| TRIPHENYLENE  | 0.1 | 0.01 |
| ANTHRACENE 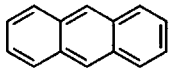 | 0.1 | 0.05 |

FIG. 6

| COMPOUND | MOLAR CONCENTRATION (M) | ELECTRIC POTENTIAL (V vs. Li/Li$^+$) |
|---|---|---|
| PHENANTHROLINE | 0.1 | 1.78 |
| 2,2'-BIPYRIDYL | 1 | 0.4 |
| BENZOPHENONE | 1 | 0.78 |
| trans-STILBENE | 0.5 | 0.3 |
| 4,4'-BIPYRIDYL | 0.1 | 1.22 |
| 3,3'-BIPYRIDYL | 0.1 | 2.5 |
| 2,4'-BIPYRIDYL | 0.1 | 0.54 |
| 2,3'-BIPYRIDYL | 0.1 | 0.58 |
| cis-STILBENE | 0.1 | 0.43 |
| ACETOPHENONE | 0.1 | 1.29 |
| PROPIOPHENONE | 0.1 | 0.42 |
| BUTYROPHENONE | 0.1 | 0.3 |
| VALEROPHENONE | 0.1 | 0.31 |
| ETHYLENEDIAMINE | 0.1 | 0.36 |

FIG. 7

| POSITIVE-ELECTRODE CHARGE-DISCHARGE MEDIATOR | 9,9'-DIPHENYL-9H,9H'-3,3'-BICARBAZOLE | 9,9'-BIS(p-TOLYL)-9H,9H'-3,3'-BICARBAZOLE | 9,9'-DIETHYL-9H,9H'-3,3'-BICARBAZOLE | TETRATHIAFULVALENE |
|---|---|---|---|---|
| POSITIVE-ELECTRODE CHARGE MEDIATOR POTENTIAL (V vs. Li/Li$^+$) | 4.09 | 4.08 | 4.03 | 3.64 |
| POSITIVE-ELECTRODE DISCHARGE MEDIATOR POTENTIAL (V vs. Li/Li$^+$) | 3.90 | 3.85 | 3.76 | 3.287 |
| NEGATIVE-ELECTRODE CHARGE MEDIATOR POTENTIAL (V vs. Li/Li$^+$) | 0.03 | 0.03 | 0.03 | 0.03 |
| NEGATIVE-ELECTRODE DISCHARGE MEDIATOR POTENTIAL (V vs. Li/Li$^+$) | 0.30 | 0.30 | 0.30 | 0.3 |
| FLOW BATTERY CHARGE VOLTAGE (V) | 4.06 | 4.05 | 4.00 | 3.61 |
| FLOW BATTERY DISCHARGE VOLTAGE (V) | 3.60 | 3.55 | 3.46 | 2.99 |
| FLOW BATTERY THEORETICAL CAPACITY DENSITY (Ah/L) | 521.53 | 521.53 | 521.53 | 353.52 |
| FLOW BATTERY THEORETICAL ENERGY DENSITY (Wh/L) | 1877.50 | 1851.42 | 1804.49 | 1055.95 |
| ELECTRICITY GENERATING ELEMENT VOLUME FILLING FACTOR | 0.60 | 0.60 | 0.60 | 0.6 |
| FLOW BATTERY ENERGY DENSITY (Wh/L) | 1126.50 | 1110.85 | 1082.69 | 633.57 |

FLOW BATTERY

BACKGROUND

1. Technical Field

The present disclosure relates to a flow battery.

2. Description of the Related Art

Japanese Unexamined Patent Application Publication (Translation of PCT Application) No. 2014-524124 discloses a redox flow battery system that includes an energy storage containing a redox mediator.

SUMMARY

There is a demand for a flow battery with a high discharge potential.

In one general aspect, the techniques disclosed here feature a flow battery that includes a first liquid containing a first electrode mediator dissolved therein, a first electrode immersed in the first liquid, a first active material immersed in the first liquid, and a first circulation mechanism that circulates the first liquid between the first electrode and the first active material, wherein the first electrode mediator includes a bicarbazyl derivative.

The flow battery can have a higher discharge potential.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a table that lists bicarbazyl derivatives usable as a first electrode mediator;

FIG. 5 is a table that lists the electric potentials of condensed aromatic compounds usable as a charge mediator;

FIG. 6 is a table that lists the electric potentials of condensed aromatic compounds usable as a discharge mediator;

FIG. 7 is a table that lists the estimated energy density of the flow battery according to the third embodiment.

DETAILED DESCRIPTION

Embodiments of the present disclosure will be described below with reference to the accompanying drawings.

First Embodiment

Figure 1:
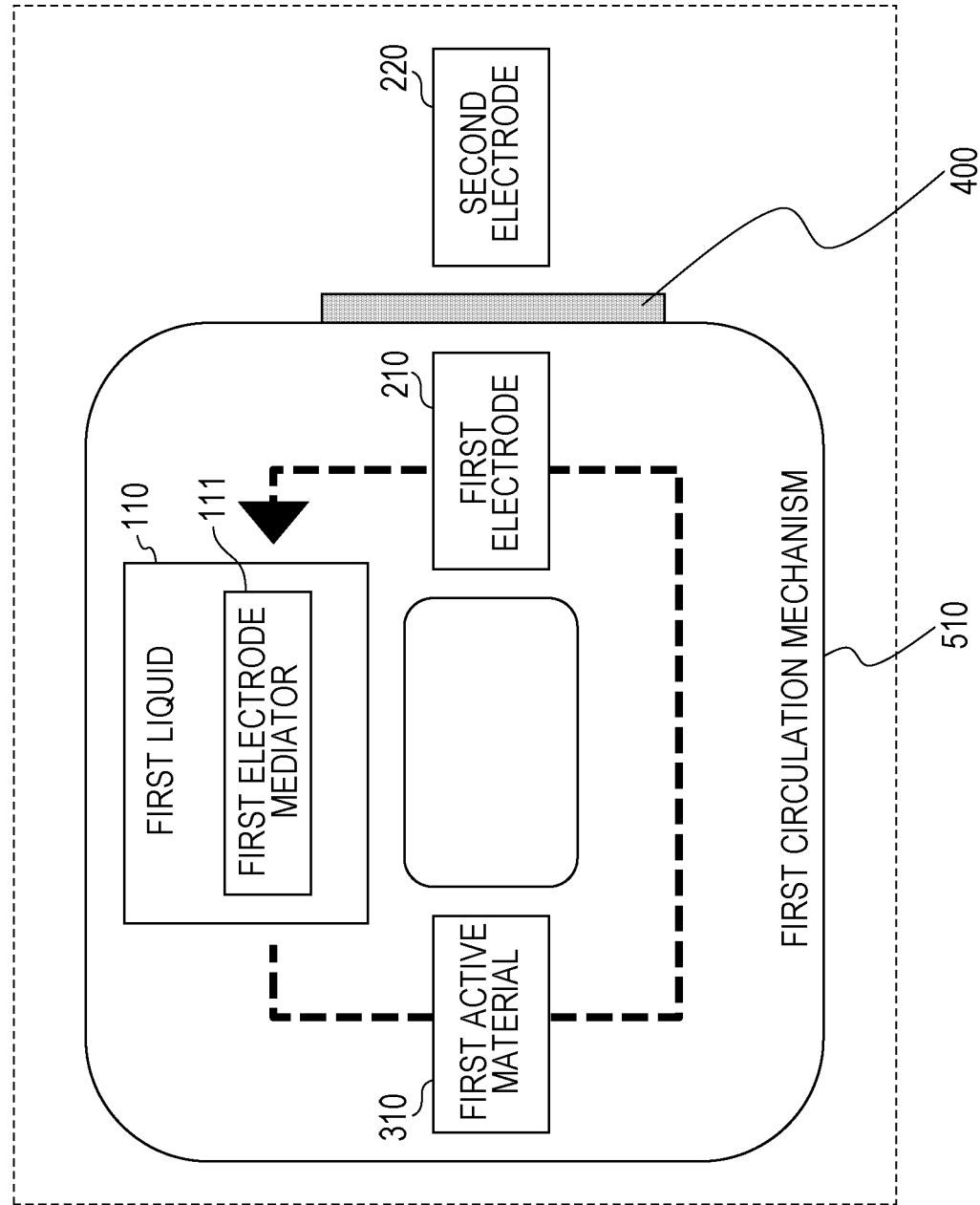
FIG. 1 is a block diagram of a flow battery according to a first embodiment.

FIG. 1 is a block diagram of a flow battery 1000 according to a first embodiment.

The flow battery 1000 according to the first embodiment includes a first liquid 110, a first electrode 210, a first active material 310, and a first circulation mechanism 510.

The first liquid 110 contains a first electrode mediator 111 dissolved therein.

The first electrode 210 is immersed in the first liquid 110.

The first active material 310 is immersed in the first liquid 110.

The first circulation mechanism 510 circulates the first liquid 110 between the first electrode 210 and the first active material 310.

The first electrode mediator 111 includes a bicarbazyl derivative.

Such a structure can provide a flow battery with a high discharge potential, high energy density, and long cycle life.

Such a structure allows a bicarbazyl derivative with a high oxidation-reduction potential (for example, approximately 4 V) to function as a charge mediator and a discharge mediator on the first electrode (for example, the positive electrode) side. Thus, an active material with a high equilibrium potential (for example, approximately 3.8 to 4.0 V vs. Li/Li$^+$) (for example, a solid positive-electrode active material with a high electric potential) can be used as the first active material 310, and the flow battery can have a higher discharge potential.

Furthermore, such a structure can provide a flow battery in which an active material is not circulated. Thus, a high-capacity active material powder can be used as the first active material 310, for example, in a charge-discharge reaction. Thus, high energy density and capacity can be achieved.

Such a structure can circulate only the first liquid 110 containing the first electrode mediator 111 dissolved therein without circulating an active material powder. This can reduce the occurrence of clogging of a pipe with the active material powder. Thus, the flow battery can have a long cycle life.

The bicarbazyl derivative in the flow battery 1000 according to the first embodiment may be represented by the following general formula (1).

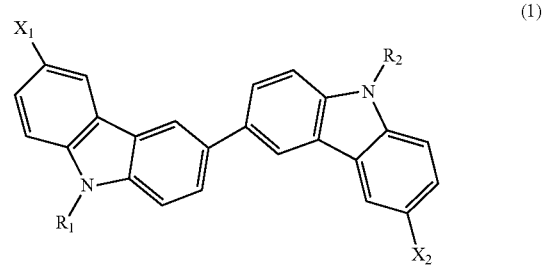

(1)

In the general formula (1), $X_1$ and $X_2$ independently denote at least one selected from the group consisting of hydrogen, fluorine, chlorine, bromine, an ether group, a cyano group, a nitro group, —NA$_2$ (A denotes a hydrocarbon group), chain saturated hydrocarbons, chain unsaturated hydrocarbons, cyclic saturated hydrocarbons, and cyclic unsaturated hydrocarbons.

$R_1$ and $R_2$ independently denote at least one selected from the group consisting of fluorine, chlorine, bromine, an ether group, a cyano group, a nitro group, —NA$_2$ (A denotes a hydrocarbon group), chain saturated hydrocarbons, chain unsaturated hydrocarbons, cyclic saturated hydrocarbons, and cyclic unsaturated hydrocarbons.

Such a structure can utilize a solid positive-electrode active material with a high electric potential. Thus, the flow battery can have a high discharge voltage.

A bicarbazyl derivative represented by the general formula (1) has substituents ($R_1$ and $R_2$) at reactive positions 9,9' of the bicarbazyl skeleton. This can prevent bonding of radical cationic species of the bicarbazyl skeleton between the positions 9,9'. This can suppress destabilization due to high reactivity of a cation radical resulting from the elimination of hydrogen at positions 9,9'. Thus, the cation radical of the bicarbazyl derivative can be stabilized. Thus, the bicarbazyl derivative can reversibly undergo two-stage oxidation-reduction reactions, unlike bicarbazyl derivatives without the substituent. Due to reversible charging and discharging and two-stage oxidation-reduction potentials, charging and discharging can be performed with one type of bicarbazyl derivative alone (the bicarbazyl derivative functions as both the charge mediator and the discharge mediator on the first electrode (for example, the positive electrode) side). The positive-electrode charge-discharge mediator can have a higher oxidation-reduction potential than known positive-electrode charge-discharge mediators (for example, tetrathiafulvalene derivatives). This allows a positive-electrode solid active material with a high electric potential to be used, and the flow battery can have a high discharge potential.

The bicarbazyl derivative in the flow battery 1000 according to the first embodiment may be represented by the following general formula (2).

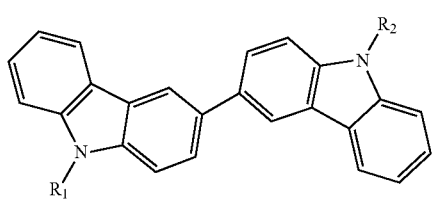

(2)

In the general formula (2), $R_1$ and $R_2$ independently denote at least one selected from the group consisting of fluorine, chlorine, bromine, an ether group, a cyano group, a nitro group, —$NA_2$ (A denotes a hydrocarbon group), chain saturated hydrocarbons, chain unsaturated hydrocarbons, cyclic saturated hydrocarbons, and cyclic unsaturated hydrocarbons.

Such a structure can provide a flow battery with a higher discharge potential.

In the flow battery 1000 according to the first embodiment, a bicarbazyl derivative represented by the general formula (1) or (2) may independently have at positions $R_1$ and $R_2$ at least one substituent selected from the group consisting of chain saturated hydrocarbons, chain unsaturated hydrocarbons, cyclic saturated hydrocarbons, cyclic unsaturated hydrocarbons, an ether group, a cyano group, a nitro group, and combinations thereof.

Such a structure can provide a flow battery with a higher discharge potential.

In the flow battery 1000 according to the first embodiment, the substituent at positions $R_1$ and $R_2$ of a bicarbazyl derivative represented by the general formula (1) or (2) may independently have at least one element (non-metallic element) selected from the group consisting of boron, nitrogen, oxygen, fluorine, silicon, phosphorus, sulfur, chlorine, bromine, and iodine.

Such a structure can provide a flow battery with a higher discharge potential.

The bicarbazyl derivative in the flow battery 1000 according to the first embodiment may be represented by the following general formula (3).

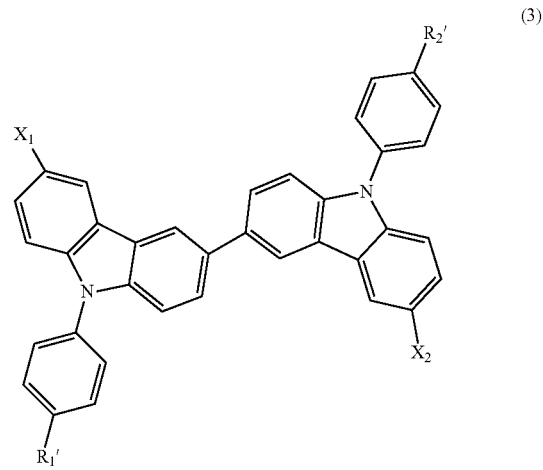

(3)

In the general formula (3), $R_1'$ and $R_2'$ independently denote at least one selected from the group consisting of hydrogen, fluorine, chlorine, bromine, an ether group, a cyano group, a nitro group, —$NA_2$ (A denotes a hydrocarbon group), chain saturated hydrocarbons, chain unsaturated hydrocarbons, cyclic saturated hydrocarbons, and cyclic unsaturated hydrocarbons.

Such a structure can provide a flow battery with a higher discharge potential.

The bicarbazyl derivative in the flow battery 1000 according to the first embodiment may be represented by the following general formula (4).

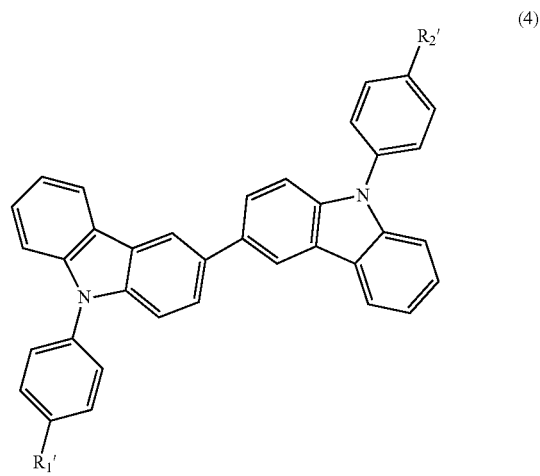

(4)

Such a structure can provide a flow battery with a higher discharge potential.

In the flow battery 1000 according to the first embodiment, a carbazole derivative represented by the general formula (1) or (3) may independently have at positions $X_1$ and $X_2$ at least one electron-withdrawing group selected from the group consisting of fluorine, chlorine, bromine, an ether group, a cyano group, a nitro group, and —NA$_2$ (A denotes a hydrocarbon group).

Such a structure may have an atom with higher electronegativity (such as fluorine or bromine) at positions $X_1$ and $X_2$. Thus, the flow battery can have a higher discharge potential.

In the flow battery 1000 according to the first embodiment, the bicarbazyl derivative may be at least one selected from the group consisting of 9,9'-diphenyl-9H,9H'-3,3'-bicarbazyl, 9,9'-bis(p-tolyl)-9H,9H'-3,3'-bicarbazyl, and 9,9'-diethyl-9H,9H'-3,3'-bicarbazyl.

Such a structure can provide a flow battery with a higher discharge potential.

FIG. 2 is a table that lists bicarbazyl derivatives usable as a first electrode mediator 111.

An electrolyte solution of 1 M electrolyte (LiBF$_4$) in a propylene carbonate solvent was prepared. "9,9'-diphenyl-9H,9H'-3,3'-bicarbazyl" was dissolved in the electrolyte solution at a concentration of 2 mM. An electrometric cell was fabricated from the electrolyte solution, a counter electrode (1×1 cm Pt foil), a working electrode (glassy carbon electrode for electrochemical measurement (φ6 mm)), and a reference electrode (silver wire (Ag/Ag$^+$)). The electrometric cell was used to measure the charge-discharge potential of "9,9'-diphenyl-9H,9H'-3,3'-bicarbazyl" by cyclic voltammetry (CV). FIG. 2 lists the measured charge-discharge potentials based on lithium metal (V vs. Li/Li$^+$). FIG. 2 also lists the charge-discharge potential of "9,9'-bis(p-tolyl)-9H,9H'-3,3'-bicarbazyl" and "9,9'-diethyl-9H,9H'-3,3'-bicarbazyl".

The bicarbazyl derivatives listed in FIG. 2 (derivatives with a substituent at positions 9,9') have two-stage oxidation-reduction potentials in the range of 3.7 to 4.1 (V vs. Li/Li$^+$). Thus, for a positive-electrode solid active material with "an equilibrium potential higher than the first oxidation-reduction potential (discharge potential) and lower than the second oxidation-reduction potential (charge potential)", one bicarbazyl derivative listed in FIG. 2 can function as a charge mediator and a discharge mediator. More specifically, the first-stage oxidation-reduction potential (first oxidation-reduction potential: E1 (V vs. Li/Li$^+$)) corresponds to the discharge potential of the mediator, and the second-stage oxidation-reduction potential (second reduction potential: E2 (V vs. Li/Li$^+$)) corresponds to the charge potential of the mediator.

The oxidation-reduction potential of a bicarbazyl derivative according to the first embodiment (a derivative with a substituent at positions 9,9') listed in FIG. 2 is higher by approximately 0.5 V or more than the oxidation-reduction potentials of known positive-electrode discharge mediators (for example, tetrathiafulvalene). For example, tetrathiafulvalene has an oxidation-reduction potential of approximately 3.2 V vs. Li/Li$^+$. By contrast, the bicarbazyl derivatives listed in FIG. 2 have an oxidation-reduction potential in the range of 3.7 to 4.1 V vs. Li/Li$^+$.

The discharge potential of a flow battery depends on the electric potential of a positive-electrode discharge mediator. Thus, the bicarbazyl derivatives according to the first embodiment, which have a high discharge potential, can provide a flow battery with a high discharge potential.

In the flow battery 1000 according to the first embodiment, the first electrode mediator 111 may contain only one bicarbazyl derivative that satisfies the conditions of the bicarbazyl derivatives according to the first embodiment.

Alternatively, in the flow battery 1000 according to the first embodiment, the first electrode mediator 111 may contain two or more bicarbazyl derivatives that satisfy the conditions of the bicarbazyl derivatives according to the first embodiment.

As described above, a bicarbazyl derivative according to the first embodiment has a first oxidation-reduction potential E1 and a second oxidation-reduction potential E2.

The equilibrium potential of the first active material 310 (V vs. Li/Li$^+$) may be higher than the first oxidation-reduction potential E1 and lower than the second oxidation-reduction potential E2.

In such a structure, the use of an active material with an equilibrium potential lower than the second oxidation-reduction potential E2 (with an electric potential lower than the second oxidation-reduction potential E2) as the first active material 310 allows a bicarbazyl derivative according to the first embodiment to function as a charge mediator. The use of an active material with an equilibrium potential higher than the first oxidation-reduction potential E1 (with an electric potential higher than the first oxidation-reduction potential E1) as the first active material 310 allows a bicarbazyl derivative according to the first embodiment to function as a discharge mediator.

In the flow battery 1000 according to the first embodiment, the first active material 310 may be a metal oxide represented by $Li_xM_yO_2$. M denotes at least one selected from the group consisting of Ni, Mn, and Co. x and y may be any number. The metal oxide has an equilibrium potential in the range of 3.8 to 4.0 V.

In the flow battery 1000 according to the first embodiment, the first active material 310 may be at least one selected from the group consisting of $LiMnO_2$, $LiMn_2O_4$, $LiCoO_2$, and $LiNiO_2$.

$LiCoO_2$ has an equilibrium potential of 3.9 V vs. Li/Li$^+$. Thus, a mediator-type positive electrode with a $LiCoO_2$ active material can be formed by using a compound with a discharge potential higher than the equilibrium potential of $LiCoO_2$ and with a charge potential lower than the equilibrium potential of $LiCoO_2$ as the first electrode mediator 111 (a charge-discharge mediator). In this case, a smaller potential difference between the equilibrium potential of $LiCoO_2$ and the charge-discharge potential of the first electrode mediator 111 results in higher charge-discharge energy efficiency. For example, a discharge potential of the first electrode mediator 111 lower than the equilibrium potential of $LiCoO_2$ and closer to the equilibrium potential of $LiCoO_2$ results in a higher discharge potential of the flow battery.

Thus, if $LiCoO_2$ is used as the first active material 310, the use of a bicarbazyl derivative listed in FIG. 2 as the first electrode mediator 111 can increase the discharge potential of the flow battery. For example, the discharge potential can be increased by approximately 0.4 to 0.5 V compared with using $LiFePO_4$ (discharge potential: approximately 3.5 V) as the first active material 310.

The first active material 310 may be a solid active material (for example, a powdered active material). If the first active material 310 is stored as an unprocessed powder in a tank, this can simplify the production and reduce production costs.

Alternatively, the first active material 310 may be a pelleted active material (for example, a powder is pelleted). If the first active material 310 is stored as pellets in a tank, this can simplify the production and reduce production costs.

The first active material 310 may be pelleted with a generally known binder (for example, poly(vinylidene difluoride), polypropylene, polyethylene, or polyimide).

The first active material 310 may be insoluble in the first liquid 110. Thus, there is provided a flow battery in which the first liquid 110 and the first electrode mediator 111 circulate, but the first active material 310 does not circulate.

In the flow battery 1000 according to the first embodiment, the first liquid 110 may be at least one selected from the group consisting of propylene carbonate (PC), ethylene carbonate (EC), γ-butyrolactone, dimethyl carbonate (DMC), ethyl methyl carbonate (EMC), and diethyl carbonate (DEC).

In the flow battery 1000 according to the first embodiment, the first liquid 110 may be an electrolyte solution containing an electrolyte in a solvent, which is the material described above usable as the first liquid 110. The electrolyte (salt) may be at least one selected from the group consisting of $LiBF_4$, $LiPF_6$, and $LiN(CF_3SO_2)_2$. The solvent may have a high dielectric constant, low reactivity with Li ions, and a potential window up to approximately 4 V.

In the flow battery 1000 according to the first embodiment, the first electrode 210 may be a positive electrode, and a second electrode 220 may be a negative electrode.

If the second electrode 220 has a relatively high electric potential, the first electrode 210 may function as a negative electrode.

Thus, the first electrode 210 may be a negative electrode, and the second electrode 220 may be a positive electrode.

In the flow battery 1000 according to the first embodiment, for example, when the first liquid 110 comes into contact with the first electrode 210, the first electrode mediator 111 is oxidized or reduced on the first electrode 210.

The first electrode 210 may have a surface acting as a reaction field for the first electrode mediator 111.

In this case, the material of the first electrode 210 may be stable in the first liquid 110 (for example, a material insoluble in the first liquid 110). The material of the first electrode 210 may also be resistant to an electrode reaction, that is, an electrochemical reaction. For example, the first electrode 210 may be formed of a metal (stainless steel, iron, copper, or nickel) or carbon.

The first electrode 210 may have a structure with an increased surface area (for example, a mesh, nonwoven fabric, surface roughened plate, or sintered porous body). Thus, the first electrode 210 may have a large specific surface area. This can promote an oxidation or reduction reaction of the first electrode mediator 111.

The second electrode 220 may include a current collector and an active material on the current collector. Thus, for example, a high-capacity active material may be used. An active material of the second electrode 220 may be a compound that reversibly adsorbs and desorbs lithium ions.

The second electrode 220 may be lithium metal. The second electrode 220 made of lithium metal can easily control dissolution and precipitation as a metal positive electrode and achieve high capacity.

The flow battery 1000 according to the first embodiment may further include a separating unit 400.

The separating unit 400 separates the first electrode 210 and the first liquid 110 from the second electrode 220.

The separating unit 400 may be a microporous film (porous body) for use in known secondary batteries.

Alternatively, the separating unit 400 may be a porous film, such as glass paper, which is a nonwoven fabric with glass fibers woven in.

Alternatively, the separating unit 400 may be a (lithium-) ion-conducting diaphragm. For example, the separating unit 400 may be an ion-exchange resin membrane (for example, a cation-exchange membrane or anion-exchange membrane) or a solid electrolyte membrane.

The first circulation mechanism 510 circulates the first liquid 110 between the first electrode 210 and the first active material 310.

Such a structure can circulate the first electrode mediator 111 together with the first liquid 110 between the first electrode 210 and the first active material 310. This can efficiently promote an oxidation reaction and a reduction reaction between materials.

The first circulation mechanism 510 may include a pipe, a tank, a pump, and a valve, for example.

A specific example of the first circulation mechanism 510 may be a structure described later in a second embodiment.

<Charge-Discharge Process>

The charge-discharge process of the flow battery 1000 according to the first embodiment will be described below.

The charge-discharge process is specifically described with the following operation example.

In the operation example, the first electrode 210 is a positive electrode made of graphite.

In the operation example, the first liquid 110 is an ether solution containing the first electrode mediator 111 dissolved therein.

In the operation example, the first electrode mediator 111 is the bicarbazyl derivative according to the first embodiment (hereinafter referred to as "Bi-Cz deriv.").

In the operation example, the first active material 310 is lithium cobalt oxide ($LiCoO_2$).

In the operation example, the second electrode 220 is a negative electrode made of lithium metal.

[Charging Process]

First, a charge reaction will be described below.

A voltage is applied between the first electrode 210 and the second electrode 220 when charging.

Reaction on Negative Electrode

Upon application of a voltage, electrons are supplied to the negative electrode, that is, the second electrode 220 from the outside of the flow battery. A reduction reaction occurs on the negative electrode, that is, the second electrode 220. Thus, the negative electrode is charged.

For example, in the operation example, the following reaction occurs.

$Li^+ + e^- \rightarrow Li$

Reaction on Positive Electrode

Upon application of a voltage, an oxidation reaction of the first electrode mediator 111 occurs on the positive electrode, that is, the first electrode 210. Thus, the first electrode mediator 111 is oxidized on the surface of the first electrode 210. Thus, electrons are released from the first electrode 210 to the outside of the flow battery.

For example, in the operation example, the following reaction occurs.

$[Bi\text{-}Cz\ deriv.] \rightarrow [Bi\text{-}Cz\ deriv.]^+ + e^-$

The first circulation mechanism 510 transfers (supplies) the first electrode mediator 111 oxidized on the first electrode 210 to the first active material 310.

The first electrode mediator 111 oxidized on the first electrode 210 is reduced by the first active material 310. In other words, the first active material 310 is oxidized by the first electrode mediator 111. Thus, the first active material 310 desorbs lithium.

For example, in the operation example, the following reaction occurs.

$LiCoO_2 + [Bi\text{-}Cz\ deriv.]^+ \rightarrow CoO_2 + Li^+ + [Bi\text{-}Cz\ deriv.]$ The first circulation mechanism 510 transfers (supplies) the first electrode mediator 111 reduced by the first active material 310 to the first electrode 210.

Thus, the first electrode mediator 111 is oxidized on the surface of the first electrode 210.

For example, in the operation example, the following reaction occurs.

$$[\text{Bi-Cz deriv.}] \rightarrow [\text{Bi-Cz deriv.}]^+ + e^-$$

Part of lithium ions (Li$^+$) thus desorbed may move to the second electrode 220 through the separating unit 400.

Thus, the first electrode mediator 111 is unchanged in the whole reaction including circulation.

Meanwhile, the first active material 310 separated from the first electrode 210 is charged.

Thus, [Bi-Cz deriv.]$^+$ acts as a charge mediator on the first electrode 210 (a first electrode side charge mediator).

In the fully charged state, the first liquid 110 contains [Bi-Cz deriv.]$^+$, and the first active material 310 is CoO$_2$. The charge potential depends on the oxidation potential in the direction toward [Bi-Cz deriv.]$^+$.

The charge reaction can continue until the first active material 310 or the second electrode 220 reaches the fully charged state.

[Discharge Process]

A discharge reaction starting from the fully charged state will be described below.

In the fully charged state, the first active material 310 and the second electrode 220 are in the charged state.

During the discharge reaction, electric power is generated between the first electrode 210 and the second electrode 220.

Reaction on Negative Electrode

An oxidation reaction occurs on the negative electrode, that is, the second electrode 220. Thus, the negative electrode is in a discharged state. Thus, electrons are released from the second electrode 220 to the outside of the flow battery.

For example, in the operation example, the following reaction occurs.

$$\text{Li} \rightarrow \text{Li}^+ + e^-$$

Reaction on Positive Electrode

When discharging the flow battery, electrons are supplied to the positive electrode, that is, the first electrode 210 from the outside of the flow battery. Thus, a reduction reaction of the first electrode mediator 111 occurs on the first electrode 210. Thus, the first electrode mediator 111 is reduced on the surface of the first electrode 210.

For example, in the operation example, the following reaction occurs.

$$[\text{Bi-Cz deriv.}]^+ + e^- \rightarrow [\text{Bi-Cz deriv.}]$$

The first circulation mechanism 510 transfers (supplies) the first electrode mediator 111 reduced on the first electrode 210 to the first active material 310.

The first electrode mediator 111 reduced on the first electrode 210 is oxidized by the first active material 310. In other words, the first active material 310 is reduced by the first electrode mediator 111. Thus, the first active material 310 adsorbs lithium.

For example, in the operation example, the following reaction occurs.

$$\text{CoO}_2 + \text{Li}^+ + [\text{Bi-Cz deriv.}] \rightarrow \text{LiCoO}_2 + [\text{Bi-Cz deriv.}]^+$$

The first circulation mechanism 510 transfers (supplies) the first electrode mediator 111 oxidized by the first active material 310 to the first electrode 210.

Thus, the first electrode mediator 111 is reduced on the surface of the first electrode 210.

For example, in the operation example, the following reaction occurs.

$$[\text{Bi-Cz deriv.}]^+ + e^- \rightarrow [\text{Bi-Cz deriv.}]$$

Part of lithium ions (Li$^+$) may be supplied from the second electrode 220 through the separating unit 400.

Thus, the first electrode mediator 111 is unchanged in the whole reaction including circulation.

Meanwhile, the first active material 310 separated from the first electrode 210 is in the discharged state.

Thus, [Bi-Cz deriv.] acts as a discharge mediator on the first electrode 210 (a first electrode side discharge mediator).

In the fully discharged state, the first liquid 110 contains [Bi-Cz deriv.], and the first active material 310 is LiCoO$_2$. The discharge potential depends on the reduction potential in the direction toward [Bi-Cz deriv.].

The discharge reaction can continue until the first active material 310 or the second electrode 220 reaches the fully discharged state.

Second Embodiment

A second embodiment will be described below. The contents described in the first embodiment are appropriately omitted to avoid overlap.

Figure 3:
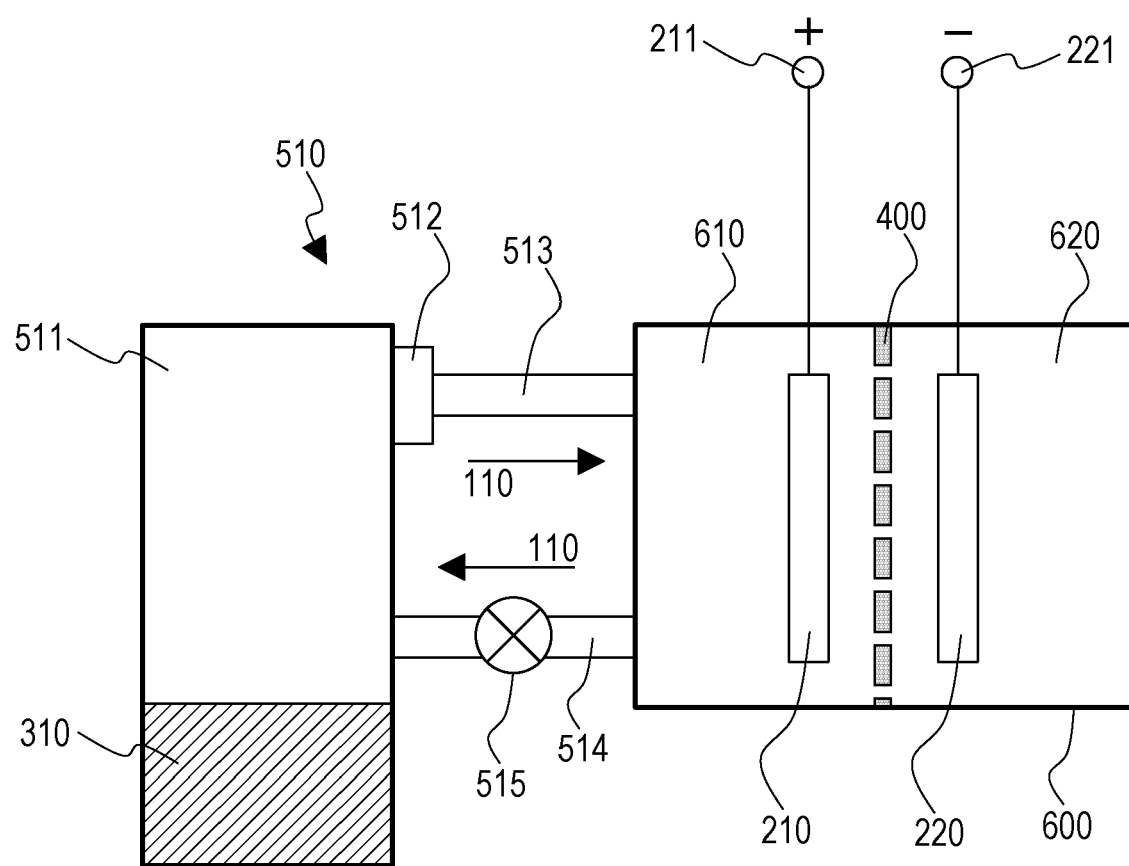
FIG. 3 is a schematic view of a flow battery according to a second embodiment.

FIG. 3 is a schematic view of a flow battery 2000 according to a second embodiment.

In addition to the components of the flow battery 1000 according to the first embodiment, the flow battery 2000 according to the second embodiment further includes the following components.

In the flow battery 2000 according to the second embodiment, the first circulation mechanism 510 includes a first container 511.

The first container 511 contains the first active material 310 and the first liquid 110.

The first circulation mechanism 510 circulates the first liquid 110 between the first electrode 210 and the first container 511.

Contact between the first active material 310 and the first liquid 110 in the first container 511 causes at least one of an oxidation reaction and a reduction reaction of the first electrode mediator 111 with the first active material 310.

In such a structure, the first liquid 110 can come into contact with the first active material 310 in the first container 511. This can increase the contact area between the first liquid 110 and the first active material 310, for example. This can also increase the contact time between the first liquid 110 and the first active material 310. This can efficiently promote an oxidation reaction and a reduction reaction of the first electrode mediator 111 with the first active material 310.

In the second embodiment, the first container 511 may be a tank.

The first container 511 may contain the first liquid 110, which contains the first electrode mediator 111 dissolved therein, in voids of the first active material 310.

As illustrated in FIG. 3, the flow battery 2000 according to the second embodiment may further include an electrochemical reaction unit 600, a positive-electrode terminal 211, and a negative-electrode terminal 221.

The electrochemical reaction unit 600 is divided into a positive-electrode chamber 610 and a negative-electrode chamber 620 by the separating unit 400.

The positive-electrode chamber 610 includes an electrode acting as a positive electrode (the first electrode 210 in FIG. 3).

The positive-electrode terminal 211 is coupled to the electrode acting as a positive electrode.

The negative-electrode chamber 620 includes an electrode acting as a negative electrode (the second electrode 220 in FIG. 3).

The negative-electrode terminal 221 is coupled to the electrode acting as a negative electrode.

The positive-electrode terminal 211 and the negative-electrode terminal 221 are coupled to a charge-discharge apparatus, for example. The charge-discharge apparatus applies a voltage between the positive-electrode terminal 211 and the negative-electrode terminal 221 or collects electric power generated between the positive-electrode terminal 211 and the negative-electrode terminal 221.

As illustrated in FIG. 3, in the flow battery 2000 according to the second embodiment, the first circulation mechanism 510 may include a pipe 514, a pipe 513, and a pump 515.

One end of the pipe 514 is coupled to one of the positive-electrode chamber 610 and the negative-electrode chamber 620 that includes the first electrode 210 (the positive-electrode chamber 610 in FIG. 3).

The other end of the pipe 514 is coupled to an inlet of the first container 511 for the first liquid 110.

One end of the pipe 513 is coupled to an outlet of the first container 511 for the first liquid 110.

The other end of the pipe 513 is coupled to one of the positive-electrode chamber 610 and the negative-electrode chamber 620 that includes the first electrode 210 (the positive-electrode chamber 610 in FIG. 3).

The pump 515 is disposed on the pipe 514, for example. Alternatively, the pump 515 may be disposed on the pipe 513.

In the flow battery 2000 according to the second embodiment, the first circulation mechanism 510 may include a first transfer prevention unit 512.

The first transfer prevention unit 512 prevents the transfer of the first active material 310.

The first transfer prevention unit 512 is disposed on the path through which the first liquid 110 flows from the first container 511 to the first electrode 210 (the pipe 513 in FIG. 3).

Such a structure can prevent the first active material 310 from flowing out of the first container 511 (for example, to the first electrode 210). Thus, the first active material 310 remains in the first container 511. Thus, the first active material 310 does not circulate in the flow battery. This can prevent clogging of the first active material 310 in a component of the first circulation mechanism 510 (for example, a pipe). This can also prevent resistive loss due to the first active material 310 flowing to the first electrode 210.

The first transfer prevention unit 512 may be disposed on the joint between the first container 511 and the pipe 513.

For example, the first transfer prevention unit 512 is a filter that filters out the first active material 310. The filter may have openings smaller than the smallest particles of the first active material 310. The filter may be formed of a material that does not react with the first active material 310 and the first liquid 110. The filter may be a glass fiber filter paper, polypropylene nonwoven fabric, polyethylene nonwoven fabric, or a metal mesh that does not react with metallic lithium.

Such a structure can prevent the first active material 310 from flowing out of the first container 511 even when the flow of the first liquid 110 causes the flow of the first active material 310 in the first container 511.

In FIG. 3, the first liquid 110 in the first container 511 is supplied to the positive-electrode chamber 610 through the first transfer prevention unit 512 and the pipe 513.

Thus, the first electrode mediator 111 dissolved in the first liquid 110 is oxidized or reduced on the first electrode 210.

Subsequently, the first liquid 110 containing the oxidized or reduced first electrode mediator 111 dissolved therein is supplied to the first container 511 through the pipe 514 and the pump 515.

Thus, the first electrode mediator 111 dissolved in the first liquid 110 undergoes at least one of an oxidation reaction and a reduction reaction with the first active material 310.

The circulation of the first liquid 110 may be controlled with the pump 515. More specifically, the supply of the first liquid 110 may be started or stopped with the pump 515, or the amount of the first liquid 110 may be controlled with the pump 515.

Alternatively, the circulation of the first liquid 110 may be controlled by another means (for example, a valve) other than the pump 515.

In FIG. 3, by way of example, the first electrode 210 is a positive electrode, and the second electrode 220 is a negative electrode.

If the second electrode 220 has a relatively high electric potential, the first electrode 210 may function as a negative electrode.

Thus, the first electrode 210 may be a negative electrode, and the second electrode 220 may be a positive electrode.

Separated by the separating unit 400, the positive-electrode chamber 610 and the negative-electrode chamber 620 may contain different electrolyte solutions (solvents).

Alternatively, the positive-electrode chamber 610 and the negative-electrode chamber 620 may contain the same electrolyte solution (solvent).

Third Embodiment

A third embodiment will be described below. The contents described in the first or second embodiment are appropriately omitted to avoid overlap.

In the third embodiment, the electrolyte solution circulates around the first electrode and around the second electrode.

Figure 4:
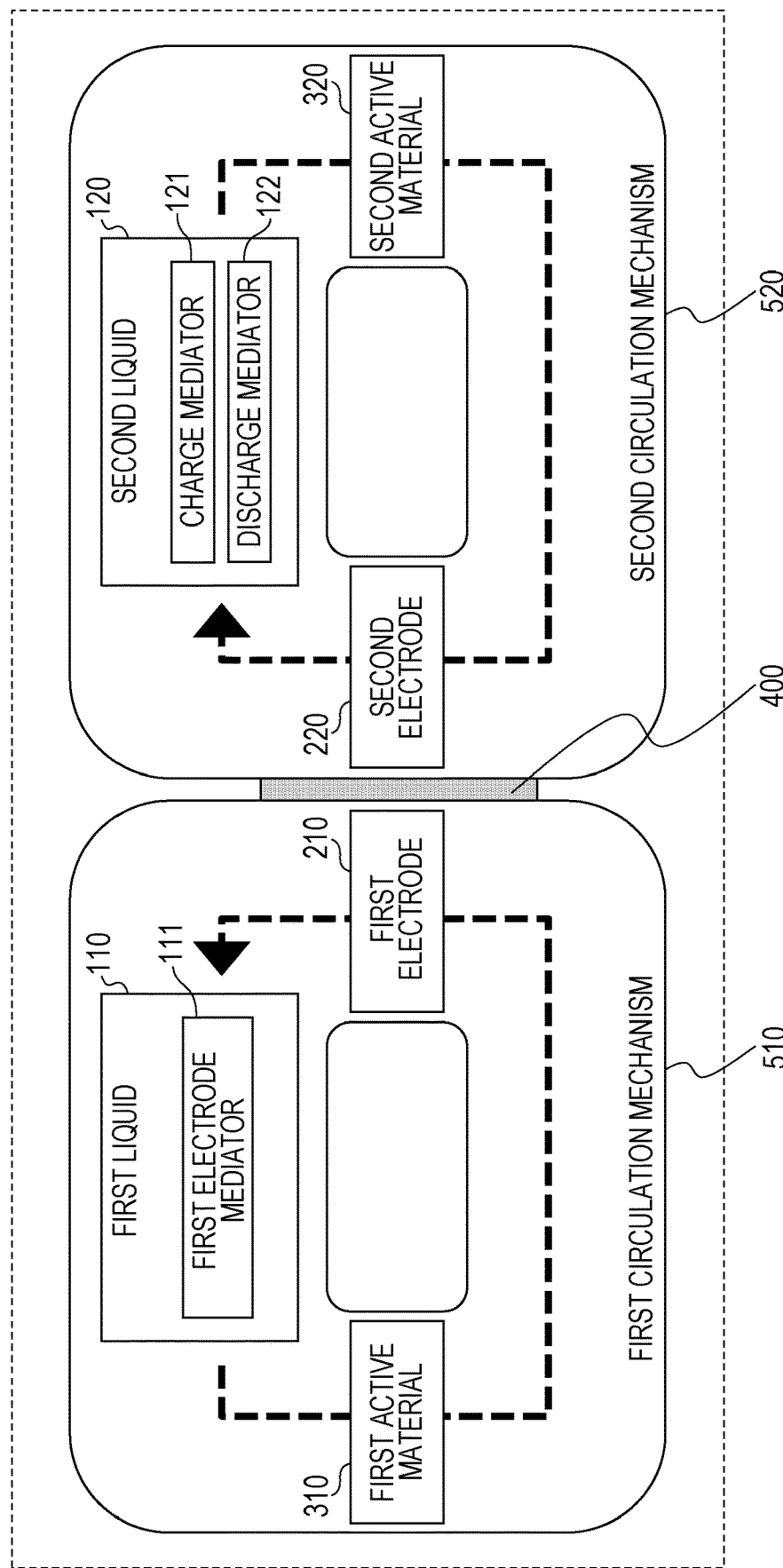
FIG. 4 is a block diagram of a flow battery according to a third embodiment.

FIG. 4 is a block diagram of a flow battery 3000 according to a third embodiment.

In addition to the components of the flow battery 1000 according to the first embodiment, the flow battery 3000 according to the third embodiment further includes the following components.

The flow battery 3000 according to the third embodiment further includes a second liquid 120, the second electrode 220, a second active material 320, and the separating unit 400.

The second liquid 120 contains the charge mediator 121 (a second electrode side charge mediator) and the discharge mediator 122 (a second electrode side discharge mediator) dissolved therein.

The second electrode 220 is immersed in the second liquid 120.

The second active material 320 is immersed in the second liquid 120.

The separating unit 400 separates the first electrode 210 and the first liquid 110 from the second electrode 220 and the second liquid 120.

The charge mediator 121 has a lower equilibrium potential than the second active material 320.

The discharge mediator 122 has a higher equilibrium potential than the second active material 320.

Such a structure can provide a flow battery with a higher battery voltage, higher energy density, and longer cycle life.

In such a structure, when the second active material 320 is an active material with a relatively low equilibrium potential (vs. Li/Li$^+$) (for example, graphite), the discharge mediator 122 may be a substance with a relatively low equilibrium potential (vs. Li/Li$^+$) (for example, a condensed aromatic compound). Thus, the negative electrode of the flow battery can have a lower electric potential. Thus, the flow battery can have a higher battery voltage (discharge voltage).

Furthermore, such a structure can provide a flow battery in which an active material is not circulated. Thus, a high-capacity active material powder can be used as the second active material 320, for example, in a charge-discharge reaction. Thus, high energy density and capacity can be achieved.

Such a structure can circulate only the second liquid 120 containing the charge mediator 121 and the discharge mediator 122 dissolved therein without circulating the active material powders. This can reduce the occurrence of clogging of a pipe with the active material powder. Thus, the flow battery can have a long cycle life.

In the flow battery 3000 according to the third embodiment, the second liquid 120 may contain lithium dissolved therein.

The second active material 320 may adsorb and desorb lithium.

When charging the flow battery 3000 (electrons are supplied from the outside of the flow battery 3000 to the second electrode 220), the charge mediator 121 may be reduced on the second electrode 220, the charge mediator 121 reduced on the second electrode 220 may be oxidized by the second active material 320, and the second active material 320 may adsorb lithium.

When discharging the flow battery 3000 (electrons are released from the second electrode 220 to the outside of the flow battery 3000), the second active material 320 on which lithium is adsorbed may reduce the discharge mediator 122, the second active material 320 may desorb lithium, and the discharge mediator 122 reduced by the second active material 320 may be oxidized on the second electrode 220.

In such a structure, the second active material 320 may reversibly adsorb and desorb lithium (for example, lithium ions). This facilitates the designing of the second active material 320. This can also further increase the capacity.

In the flow battery 3000 according to the third embodiment, when charging, the discharge mediator 122 may be reduced on the second electrode 220.

When discharging, the charge mediator 121 may be oxidized on the second electrode 220.

Such a structure can further increase the energy density and capacity. More specifically, if the discharge mediator 122 is reduced on the second electrode 220 when charging, the amount of the discharge mediator 122 oxidized on the second electrode 220 when discharging can be increased. Furthermore, if the charge mediator 121 is oxidized on the second electrode 220 when discharging, the amount of the charge mediator 121 reduced on the second electrode 220 when charging can be increased. This can increase charge-discharge capacity.

In the flow battery 3000 according to the third embodiment, the charge mediator 121 and the discharge mediator 122 may be condensed aromatic compounds.

The second liquid 120 containing a condensed aromatic compound dissolved therein causes a solvated electron of lithium to be released and thereby dissolves the lithium as a cation.

Such a structure can provide the charge mediator 121 and the discharge mediator 122 with a low electric potential. A solution (for example, an ether solution) containing a condensed aromatic compound can dissolve lithium (for example, lithium metal). Lithium tends to release an electron and become a cation. Thus, lithium donates an electron to the condensed aromatic compound in the solution and dissolves in the solution as a cation. The condensed aromatic compound that accepts the electron solvates with the electron. The condensed aromatic compound solvated with the electron behaves as an anion. Thus, the solution containing the condensed aromatic compound is ion conductive by itself. The solution containing the condensed aromatic compound contains the equivalent amounts of Li cations and electrons. Thus, the solution containing the condensed aromatic compound can be highly reductive (that is, have a low electric potential).

For example, an electrode that does not react with lithium immersed in the second liquid 120 containing a condensed aromatic compound dissolved therein has a much lower electric potential than lithium metal. The electric potential depends on the degree of solvation between the condensed aromatic compound and an electron (the type of condensed aromatic compound). Examples of the condensed aromatic compound with a low electric potential include phenanthrene, biphenyl, O-terphenyl, triphenylene, anthracene, phenanthroline, 2,2'-bipyridyl, benzophenone, trans-stilbene, 4,4'-bipyridyl, 3,3'-bipyridyl, 2,4'-bipyridyl, 2,3'-bipyridyl, cis-stilbene, acetophenone, propiophenone, butyrophenone, valerophenone, and ethylenediamine.

In the flow battery 3000 according to the third embodiment, the charge mediator 121 may be at least one selected from the group consisting of phenanthrene, biphenyl, O-terphenyl, triphenylene, and anthracene.

Such a structure can provide the charge mediator 121 with a low electric potential. More specifically, a charge mediator with a lower electric potential (vs. Li/Li$^+$) than the second active material 320 (for example, graphite) can be obtained.

In the flow battery 3000 according to the third embodiment, the discharge mediator 122 may be at least one selected from the group consisting of phenanthroline, 2,2'-bipyridyl, benzophenone, trans-stilbene, 4,4'-bipyridyl, 3,3'-bipyridyl, 2,4'-bipyridyl, 2,3'-bipyridyl, cis-stilbene, acetophenone, propiophenone, butyrophenone, valerophenone, and ethylenediamine.

Such a structure can provide the discharge mediator 122 with a high electric potential. More specifically, the discharge mediator 122 with a higher electric potential (vs. Li/Li$^+$) than the second active material 320 (for example, graphite) can be obtained.

In the flow battery 3000 according to the third embodiment, the discharge mediator 122 may be at least one selected from the group consisting of 2,2'-bipyridyl, stilbene, 2,4'-bipyridyl, 2,3'-bipyridyl, cis-stilbene, propiophenone, butyrophenone, valerophenone, and ethylenediamine.

Such a structure can decrease the equilibrium potential (vs. Li/Li$^+$) of the discharge mediator 122. Thus, the negative electrode of the flow battery can have a lower electric potential. Thus, the flow battery can have a higher battery voltage (discharge voltage).

In the flow battery 3000 according to the third embodiment, the second liquid 120 may be an ether solution.

In such a structure, the second liquid 120 can be an electrolyte solution containing the charge mediator 121 and the discharge mediator 122. More specifically, the solvent of the charge mediator 121 and the discharge mediator 122 can be an electronically non-conductive ether solution, and the ether solution itself can have the properties of an electrolyte solution.

The ether may be tetrahydrofuran (THF), 2-methyltetrahydrofuran (2MeTHF), dimethoxyethane (DME), 1,3-dioxane (1,3DO), or 4-methyl-1,3-dioxane (4Me1,3DO).

In the flow battery 3000 according to the third embodiment, the second active material 320 may be graphite.

Such a structure can decrease the equilibrium potential (vs. $Li/Li^+$) of the second active material 320. Thus, the discharge mediator 122 can be a substance with a relatively low equilibrium potential (vs. $Li/Li^+$) (for example, a condensed aromatic compound). Thus, the negative electrode of the flow battery can have a lower electric potential. Thus, the flow battery can have a high battery voltage (discharge voltage).

In the third embodiment, graphite of the second active material 320 on which lithium is adsorbed (a graphite interlayer compound produced when charging) may have a composition of at least one of $C_{24}Li$, $C_{18}Li$, $C_{12}Li$, and $C_6Li$.

When the second active material 320 is graphite ($C_6Li$), charging involves complete reduction by lithium (graphite adsorbs lithium to yield $C_6Li$). $C_6Li$ has an electric potential of approximately 0.2 V vs. $Li/Li^+$. Thus, a mediator-type negative electrode can be formed by using a condensed aromatic compound with a lower electric potential than $C_6Li$ as a charge mediator and a condensed aromatic compound with a higher electric potential than $C_6Li$ as a discharge mediator.

FIG. 5 is a table that lists the electric potentials of condensed aromatic compounds usable as a charge mediator 121.

FIG. 6 is a table that lists the electric potentials of condensed aromatic compounds usable as a discharge mediator 122.

A 2×2 cm copper foil is covered with a polypropylene microporous separator, which is covered with a large amount of lithium metal foil. A tab is attached to the copper foil and lithium metal. Subsequently, a laminate exterior is provided. After pouring 2MeTHF in which a condensed aromatic compound is dissolved at a molar concentration (M) listed in FIGS. 5 and 6, the laminate exterior is hermetically sealed by heat. Thus, an electrometric cell for each condensed aromatic compound is prepared. FIGS. 5 and 6 list the electric potentials (V vs. $Li/Li^+$) based on lithium metal measured with the electrometric cells. Although 2MeTHF can be used in this measurement, another ether may also be used.

The charge mediator 121 cannot dissolve Li of $C_6Li$. By contrast, the discharge mediator 122 can dissolve Li of $C_6Li$. This difference results from the difference between the electric potential of $C_6Li$ and the electric potentials of these lithium metal solutions. Those with a higher electric potential than $C_6Li$ (approximately 0.2 V vs. $Li/Li^+$) can dissolve Li of $C_6Li$. By contrast, those with a lower electric potential than $C_6Li$ (approximately 0.2 V vs. $Li/Li^+$) cannot dissolve Li of $C_6Li$.

Thus, those with a lower electric potential than $C_6Li$ can be used as the charge mediator 121. Those with a higher electric potential than $C_6Li$ can be used as the discharge mediator 122.

A smaller potential difference between the condensed aromatic compound and the second active material 320 results in higher charge-discharge energy efficiency. When the second active material 320 is graphite ($C_6Li$), therefore, the charge mediator 121 may be phenanthrene, triphenylene, or biphenyl. The discharge mediator 122 may be trans-stilbene, butyrophenone, valerophenone, or ethylenediamine. This can further increase charge-discharge energy efficiency.

Unlike Li ions, the ether may not be intercalated into graphite. No co-intercalation of Li and the ether in graphite can increase capacity density.

The second active material 320 may be a solid active material (for example, a powdered active material). If the second active material 320 is stored as an unprocessed powder in a tank, this can simplify the production and reduce production costs.

Alternatively, the second active material 320 may be a pelleted active material (for example, a powder is pelleted). If the second active material 320 is stored as pellets in a tank, this can simplify the production and reduce production costs.

The second active material 320 may be pelleted with a generally known binder (for example, poly(vinylidene difluoride), polypropylene, polyethylene, or polyimide).

The second active material 320 may be insoluble in the second liquid 120. Thus, there is provided a flow battery in which the charge mediator 121 and the discharge mediator 122 as well as the second liquid 120 circulate, but the second active material 320 does not circulate.

In the flow battery 3000 according to the third embodiment, the second electrode 220 may be a negative electrode, and the first electrode 210 may be a positive electrode.

If the first electrode 210 has a relatively low electric potential, the second electrode 220 may function as a positive electrode.

Thus, the second electrode 220 may be a positive electrode, and the first electrode 210 may be a negative electrode.

In the flow battery 3000 according to the third embodiment, for example, when the second liquid 120 comes into contact with the second electrode 220, the charge mediator 121 and the discharge mediator 122 are oxidized or reduced on the second electrode 220. For example, when the second liquid 120 comes into contact with the second active material 320, the second active material 320 causes a reduction reaction of the discharge mediator 122 or an oxidation reaction of the charge mediator 121.

The second electrode 220 may have a surface that acts as a reaction field for the charge mediator 121 and the discharge mediator 122.

In this case, the material of the second electrode 220 may be stable in the second liquid 120 (for example, a material insoluble in the second liquid 120). The material of the second electrode 220 may also be resistant to an electrode reaction, that is, an electrochemical reaction. For example, the second electrode 220 may be formed of a metal (stainless steel, iron, copper, or nickel) or carbon.

The second electrode 220 may have a structure with an increased surface area (for example, a mesh, nonwoven fabric, surface roughened plate, or sintered porous body). Thus, the second electrode 220 may have a large specific surface area. This can promote an oxidation or reduction reaction of the charge mediator 121 and the discharge mediator 122.

The flow battery 3000 according to the third embodiment may further include a second circulation mechanism 520.

The second circulation mechanism 520 circulates the second liquid 120 between the second electrode 220 and the second active material 320.

Such a structure can circulate the charge mediator 121 and the discharge mediator 122 together with the second liquid 120 between the second electrode 220 and the second active material 320. This can efficiently promote an oxidation reaction and a reduction reaction between materials.

The second circulation mechanism 520 may include a pipe, a tank, a pump, and a valve, for example.

A specific example of the second circulation mechanism 520 may be a structure described later in a fourth embodiment.

<Charge-Discharge Process>

The charge-discharge process of the flow battery 3000 according to the third embodiment will be described below.

The charge-discharge process is specifically described with the following operation example.

In the operation example, the first electrode 210 is a positive electrode made of graphite.

In the operation example, the first liquid 110 is an ether solution containing the first electrode mediator 111 dissolved therein.

In the operation example, the first electrode mediator 111 is the bicarbazyl derivative according to the first embodiment (hereinafter referred to as "Bi-Cz deriv.").

In the operation example, the first active material 310 is lithium cobalt oxide (LiCoO$_2$).

In the operation example, the second electrode 220 is a negative electrode made of stainless steel.

In the operation example, the second liquid 120 is an ether solution containing the charge mediator 121 and the discharge mediator 122 dissolved therein.

In the operation example, the charge mediator 121 on the side of the second electrode 220 is a condensed aromatic compound (hereinafter referred to as ChMd).

In the operation example, the discharge mediator 122 on the side of the second electrode 220 is a condensed aromatic compound (hereinafter referred to as DchMd).

In the operation example, the second active material 320 is graphite (C$_6$Li).

In the operation example, the separating unit 400 is a lithium ion conductive solid electrolyte membrane.

[Charging Process]

First, a charge reaction will be described below.

A voltage is applied between the first electrode 210 and the second electrode 220 when charging.

Reaction on Negative Electrode

Upon application of a voltage, electrons are supplied to the negative electrode, that is, the second electrode 220 from the outside of the flow battery. This causes a reduction reaction of the charge mediator 121 and the discharge mediator 122 on the second electrode 220.

For example, in the operation example, the following reaction occurs.

$$ChMd + Li^+ + e^- \rightarrow ChMd.Li$$

$$DchMd + Li^+ + e^- \rightarrow DchMd.Li$$

The second circulation mechanism 520 transfers (supplies) the charge mediator 121 reduced on the second electrode 220 to the second active material 320.

The charge mediator 121 reduced on the second electrode 220 is oxidized by the second active material 320. In other words, the second active material 320 is reduced by the charge mediator 121. Thus, the second active material 320 adsorbs lithium and becomes C$_6$Li.

For example, in the operation example, the following reaction occurs.

$$6C + ChMd.Li \rightarrow C_6Li + ChMd$$

The second circulation mechanism 520 transfers (supplies) the charge mediator 121 oxidized by the second active material 320 to the second electrode 220.

Thus, the charge mediator 121 is unchanged in the whole reaction including circulation.

Meanwhile, the second active material 320 separated from the second electrode 220 is charged.

Reaction on Positive Electrode

Upon application of a voltage, an oxidation reaction of the first electrode mediator 111 occurs on the positive electrode, that is, the first electrode 210. Thus, the first electrode mediator 111 is oxidized on the surface of the first electrode 210. Thus, electrons are released from the first electrode 210 to the outside of the flow battery.

For example, in the operation example, the following reaction occurs.

$$[\text{Bi-Cz deriv.}] \rightarrow [\text{Bi-Cz deriv.}]^+ + e^-$$

The first circulation mechanism 510 transfers (supplies) the first electrode mediator 111 oxidized on the first electrode 210 to the first active material 310.

The first electrode mediator 111 oxidized on the first electrode 210 is reduced by the first active material 310. In other words, the first active material 310 is oxidized by the first electrode mediator 111. Thus, the first active material 310 desorbs lithium.

For example, in the operation example, the following reaction occurs.

$$LiCoO_2 + [\text{Bi-Cz deriv.}]^+ \rightarrow CoO_2 + Li^+ + [\text{Bi-Cz deriv.}]$$

The first circulation mechanism 510 transfers (supplies) the first electrode mediator 111 reduced by the first active material 310 to the first electrode 210.

Thus, the first electrode mediator 111 is oxidized on the surface of the first electrode 210.

For example, in the operation example, the following reaction occurs.

$$[\text{Bi-Cz deriv.}] \rightarrow [\text{Bi-Cz deriv.}]^+ + e^-$$

Part of lithium ions (Li$^+$) thus desorbed may move to the second electrode 220 through the separating unit 400.

Thus, the first electrode mediator 111 is unchanged in the whole reaction including circulation.

Meanwhile, the first active material 310 separated from the first electrode 210 is charged.

Thus, [Bi-Cz deriv.]$^+$ acts as a charge mediator on the first electrode 210 (a first electrode side charge mediator).

In the fully charged state, the first liquid 110 contains [Bi-Cz deriv.]$^+$, and the first active material 310 is LiCoO$_2$. The charge potential depends on the oxidation potential in the direction toward [Bi-Cz deriv.]$^+$.

The charge reaction can continue until the first active material 310 or the second active material 320 reaches the fully charged state.

[Discharge Process]

A discharge reaction starting from the fully charged state will be described below.

In the fully charged state, the first active material 310 and the second active material 320 are in the charged state.

During the discharge reaction, electric power is generated between the first electrode 210 and the second electrode 220.

Reaction on Negative Electrode

Battery discharge causes an oxidation reaction of the charge mediator 121 and the discharge mediator 122 on the negative electrode, that is, the second electrode 220. Thus, electrons are released from the second electrode 220 to the outside of the flow battery.

For example, in the operation example, the following reaction occurs.

DchMd.Li→DchMd+Li$^+$+e$^-$

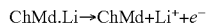
ChMd.Li→ChMd+Li$^+$+e$^-$

The second circulation mechanism 520 transfers (supplies) the discharge mediator 122 oxidized on the second electrode 220 to the second active material 320.

The discharge mediator 122 oxidized on the second electrode 220 is reduced by the second active material 320. In other words, the second active material 320 is oxidized by the discharge mediator 122. Thus, the second active material 320 desorbs lithium.

For example, in the operation example, the following reaction occurs.

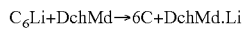
C$_6$Li+DchMd→6C+DchMd.Li

The second circulation mechanism 520 transfers (supplies) the discharge mediator 122 reduced by the second active material 320 to the second electrode 220.

Thus, the discharge mediator 122 is unchanged in the whole reaction including circulation.

Meanwhile, the second active material 320 separated from the second electrode 220 is in the discharged state.

Reaction on Positive Electrode

When discharging the flow battery, electrons are supplied to the positive electrode, that is, the first electrode 210 from the outside of the flow battery. Thus, a reduction reaction of the first electrode mediator 111 occurs on the first electrode 210. Thus, the first electrode mediator 111 is reduced on the surface of the first electrode 210.

For example, in the operation example, the following reaction occurs.

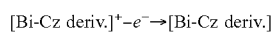
[Bi-Cz deriv.]$^+$−e$^-$→[Bi-Cz deriv.]

The first circulation mechanism 510 transfers (supplies) the first electrode mediator 111 reduced on the first electrode 210 to the first active material 310.

The first electrode mediator 111 reduced on the first electrode 210 is oxidized by the first active material 310. In other words, the first active material 310 is reduced by the first electrode mediator 111. Thus, the first active material 310 adsorbs lithium.

For example, in the operation example, the following reaction occurs.

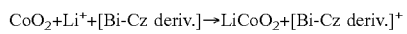
CoO$_2$+Li$^+$+[Bi-Cz deriv.]→LiCoO$_2$+[Bi-Cz deriv.]$^+$

The first circulation mechanism 510 transfers (supplies) the first electrode mediator 111 oxidized by the first active material 310 to the first electrode 210.

Thus, the first electrode mediator 111 is reduced on the surface of the first electrode 210.

For example, in the operation example, the following reaction occurs.

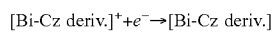
[Bi-Cz deriv.]$^+$+e$^-$→[Bi-Cz deriv.]

Part of lithium ions (Li$^+$) may be supplied from the second electrode 220 through the separating unit 400.

Thus, the first electrode mediator 111 is unchanged in the whole reaction including circulation.

Meanwhile, the first active material 310 separated from the first electrode 210 is in the discharged state.

Thus, [Bi-Cz deriv.] acts as a discharge mediator on the first electrode 210 (a first electrode side discharge mediator).

In the fully discharged state, the first liquid 110 contains [Bi-Cz deriv.], and the first active material 310 is LiCoO$_2$. The discharge potential depends on the reduction potential in the direction toward [Bi-Cz deriv.].

The discharge reaction can continue until the first active material 310 or the second active material 320 reaches the fully discharged state.

<Estimation of Energy Density>

The estimated energy density of the flow battery 3000 according to the third embodiment will be described below.

FIG. 7 is a table that lists the estimated energy density of the flow battery 3000 according to the third embodiment.

FIG. 7 lists the estimated energy densities under the conditions of the operation example of the flow battery 3000 according to the third embodiment. Each of the compounds listed in FIG. 2 is used as the first electrode mediator 111 (a positive-electrode charge-discharge mediator). The charge mediator 121 on the negative electrode is phenanthrene, and the discharge mediator 122 on the negative electrode is trans-stilbene.

In FIG. 7, in the calculation example in which tetrathiafulvalene is used as the first electrode mediator 111 (a positive-electrode charge-discharge mediator), the positive-electrode solid active material is LiFePO$_4$.

As shown in FIG. 7, the flow battery can have an energy density of approximately 1082 to 1127 Wh/L when a bicarbazyl derivative according to the first embodiment is used as the first electrode mediator 111.

By contrast, the theoretical energy densities of known flow batteries (utilizing vanadium) are approximately 38 Wh/L. Thus, the flow batteries according to the present disclosure have significantly higher theoretical energy densities than known flow batteries.

As shown in FIG. 7, when tetrathiafulvalene is used as the first electrode mediator 111, LiFePO$_4$ should be used as the positive-electrode solid active material. Thus, the flow battery has an energy density of approximately 633 Wh/L. This result shows that a flow battery utilizing a bicarbazyl derivative according to the first embodiment has a higher theoretical energy density than those utilizing tetrathiafulvalene or a derivative thereof.

Fourth Embodiment

A fourth embodiment will be described below. The contents described in the first to third embodiments are appropriately omitted to avoid overlap.

Figure 8:
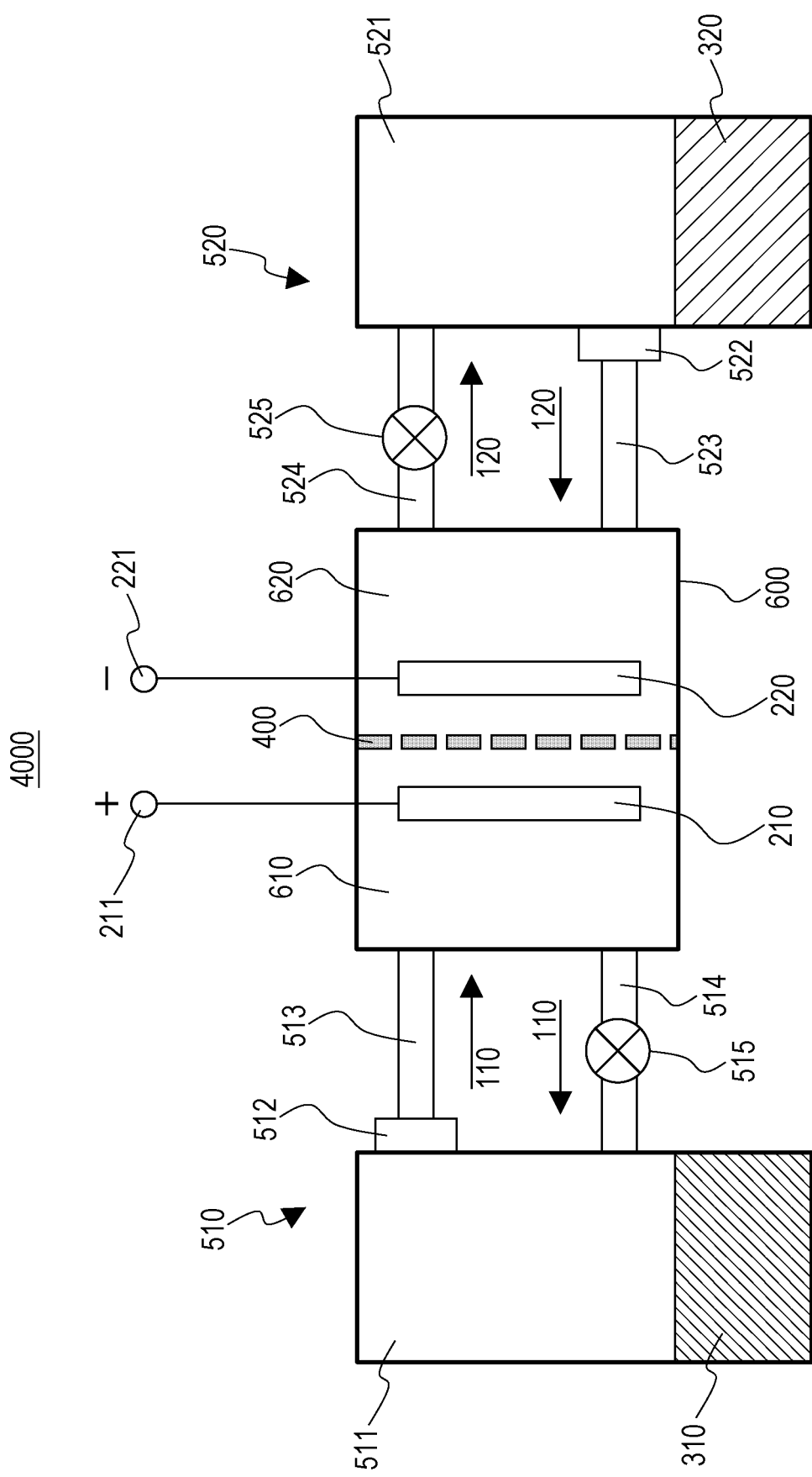
FIG. 8 is a schematic view of a flow battery according to a fourth embodiment.

FIG. 8 is a schematic view of a flow battery 4000 according to a fourth embodiment; and In addition to the components of the flow battery 3000 according to the third embodiment, the flow battery 4000 according to the fourth embodiment further includes the following components.

First, the flow battery 4000 according to the fourth embodiment includes the first circulation mechanism 510 described in the second embodiment.

The flow battery 4000 according to the fourth embodiment further includes the electrochemical reaction unit 600, the positive-electrode terminal 211, and the negative-electrode terminal 221 described in the second embodiment.

The flow battery 4000 according to the fourth embodiment further includes the second circulation mechanism 520.

The second circulation mechanism 520 includes a second container 521.

The second container 521 contains the second active material 320 and the second liquid 120.

The second circulation mechanism 520 circulates the second liquid 120 between the second electrode 220 and the second container 521.

In the second container 521, contact between the second active material 320 and the second liquid 120 causes at least one of an oxidation reaction of the charge mediator 121 with the second active material 320 and a reduction reaction of the discharge mediator 122 with the second active material 320.

In such a structure, the second liquid 120 can come into contact with the second active material 320 in the second container 521. This can increase the contact area between the second liquid 120 and the second active material 320, for example. This can also increase the contact time between the second liquid 120 and the second active material 320. This can efficiently promote an oxidation reaction of the charge mediator 121 with the second active material 320 and a reduction reaction of the discharge mediator 122 with the second active material 320.

In the fourth embodiment, the second container 521 may be a tank.

The second container 521 may contain the second liquid 120, which contains the charge mediator 121 and the discharge mediator 122 dissolved therein, in voids of the second active material 320.

As illustrated in FIG. 8, in the flow battery 4000 according to the fourth embodiment, the second circulation mechanism 520 may include a pipe 523, a pipe 524, and a pump 525.

One end of the pipe 524 is coupled to one of the positive-electrode chamber 610 and the negative-electrode chamber 620 that includes the second electrode 220 (the negative-electrode chamber 620 in FIG. 8).

The other end of the pipe 524 is coupled to an inlet of the second container 521 for the second liquid 120.

One end of the pipe 523 is coupled to an outlet of the second container 521 for the second liquid 120.

The other end of the pipe 523 is coupled to one of the positive-electrode chamber 610 and the negative-electrode chamber 620 that includes the second electrode 220 (the negative-electrode chamber 620 in FIG. 8).

The pump 525 is disposed on the pipe 524, for example. Alternatively, the pump 525 may be disposed on the pipe 523.

In the flow battery 4000 according to the fourth embodiment, the second circulation mechanism 520 may include a second transfer prevention unit 522.

The second transfer prevention unit 522 prevents the transfer of the second active material 320.

The second transfer prevention unit 522 is disposed on the path through which the second liquid 120 flows from the second container 521 to the second electrode 220 (the pipe 523 in FIG. 8).

Such a structure can prevent the second active material 320 from flowing out of the second container 521 (for example, to the second electrode 220). Thus, the second active material 320 remains in the second container 521. Thus, the second active material 320 does not circulate in the flow battery. This can prevent clogging of the second active material 320 in a component of the second circulation mechanism 520 (for example, a pipe). This can also prevent resistive loss due to the second active material 320 flowing to the second electrode 220.

The second transfer prevention unit 522 may be disposed on the joint between the second container 521 and the pipe 523.

For example, the second transfer prevention unit 522 is a filter that filters out the second active material 320. The filter may have openings smaller than the smallest particles of the second active material 320. The filter may be formed of a material that does not react with the second active material 320 and the second liquid 120. The filter may be a glass fiber filter paper, polypropylene nonwoven fabric, polyethylene nonwoven fabric, or a metal mesh that does not react with metallic lithium.

Such a structure can prevent the second active material 320 from flowing out of the second container 521 even when the flow of the second liquid 120 causes the flow of the second active material 320 in the second container 521.

In FIG. 8, the second liquid 120 in the second container 521 is supplied to the negative-electrode chamber 620 through the second transfer prevention unit 522 and the pipe 523.

Thus, the charge mediator 121 and the discharge mediator 122 dissolved in the second liquid 120 is oxidized or reduced on the second electrode 220.

Subsequently, the second liquid 120 containing the oxidized or reduced charge mediator 121 and discharge mediator 122 dissolved therein is supplied to the second container 521 through the pipe 524 and the pump 525.

Thus, the charge mediator 121 and the discharge mediator 122 dissolved in the second liquid 120 undergo at least one of an oxidation reaction of the charge mediator 121 with the second active material 320 and a reduction reaction of the discharge mediator 122 with the second active material 320.

The circulation of the second liquid 120 may be controlled with the pump 525. More specifically, the supply of the second liquid 120 may be started or stopped with the pump 525, or the amount of the second liquid 120 may be controlled with the pump 525.

Alternatively, the circulation of the second liquid 120 may be controlled by another means (for example, a valve) other than the pump 525.

In FIG. 8, by way of example, the first electrode 210 is a positive electrode, and the second electrode 220 is a negative electrode.

If the first electrode 210 has a relatively low electric potential, the second electrode 220 may function as a positive electrode.

Thus, the second electrode 220 may be a positive electrode, and the first electrode 210 may be a negative electrode.

The constituents of the first to fourth embodiments may be appropriately combined.

A flow battery according to the present disclosure can be suitable for charge storage devices and charge storage systems, for example.

What is claimed is:

1. A flow battery comprising:
   a first liquid containing a first electrode mediator dissolved therein;
   a first electrode immersed in the first liquid;
   a first active material immersed in the first liquid; and
   a first circulation mechanism that circulates the first liquid between the first electrode and the first active material,
   wherein the first electrode mediator consists of a bicarbazyl derivative.

2. The flow battery according to claim 1, wherein the bicarbazyl derivative is represented by the following general formula (1), (1)

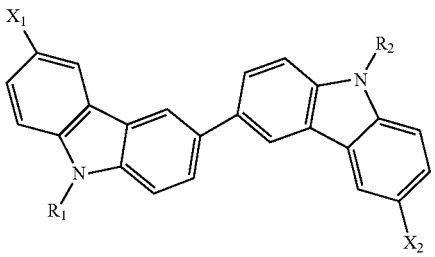

wherein $X_1$ and $X_2$ independently denote at least one selected from the group consisting of hydrogen, fluorine, chlorine, bromine, an ether group, a cyano group, a nitro group, —$NA_2$ (A denotes a hydrocarbon group), chain saturated hydrocarbons, chain unsaturated hydrocarbons, cyclic saturated hydrocarbons, and cyclic unsaturated hydrocarbons, and $R_1$ and $R_2$ independently denote at least one selected from the group consisting of fluorine, chlorine, bromine, an ether group, a cyano group, a nitro group, —$NA_2$ (A denotes a hydrocarbon group), chain saturated hydrocarbons, chain unsaturated hydrocarbons, cyclic saturated hydrocarbons, and cyclic unsaturated hydrocarbons.

3. The flow battery according to claim 2, wherein the bicarbazyl derivative is represented by the following general formula (2).

(2)

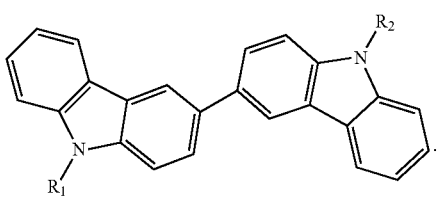

4. The flow battery according to claim 2, wherein at least one substituent selected from the group consisting of chain saturated hydrocarbons, chain unsaturated hydrocarbons, cyclic saturated hydrocarbons, cyclic unsaturated hydrocarbons, an ether group, a cyano group, a nitro group, and combinations thereof is independently disposed at positions $R_1$ and $R_2$.

5. The flow battery according to claim 2, wherein the bicarbazyl derivative is represented by the following general formula (3), (3)

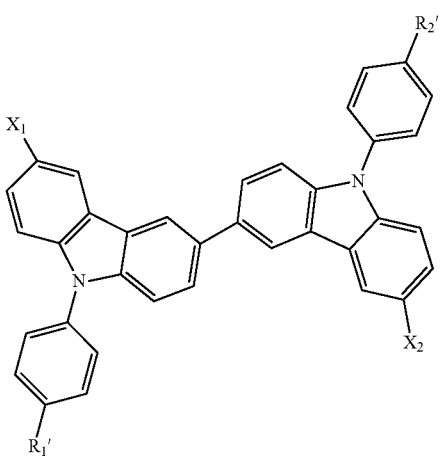

wherein $R_1'$ and $R_2'$ independently denote at least one selected from the group consisting of hydrogen, fluorine, chlorine, bromine, an ether group, a cyano group, a nitro group, —$NA_2$ (A denotes a hydrocarbon group), chain saturated hydrocarbons, chain unsaturated hydrocarbons, cyclic saturated hydrocarbons, and cyclic unsaturated hydrocarbons.

6. The flow battery according to claim 5, wherein the bicarbazyl derivative is represented by the following general formula (4).

(4)

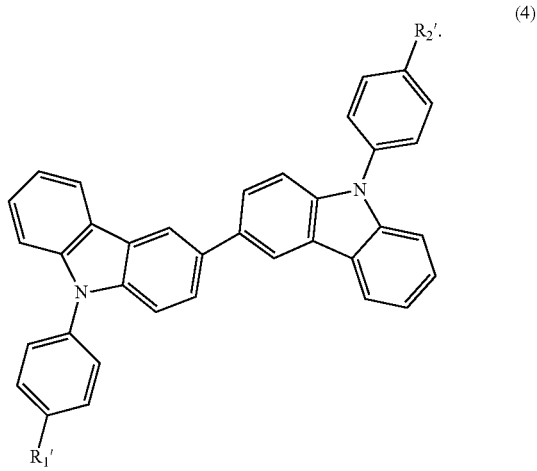

7. The flow battery according to claim 2, wherein at least one electron-withdrawing group selected from the group consisting of fluorine, chlorine, bromine, an ether group, a cyano group, a nitro group, and —$NA_2$ is independently disposed at positions $X_1$ and $X_2$.

8. The flow battery according to claim 1, wherein the bicarbazyl derivative is at least one selected from the group consisting of 9,9'-diphenyl-9H,9H'-3,3'-bicarbazyl, 9,9'-bis(p-tolyl)-9H,9H'-3,3'-bicarbazyl, and 9,9'-diethyl-9H,9H'-3,3'-bicarbazyl.

9. The flow battery according to claim 1, wherein
the bicarbazyl derivative has a first oxidation-reduction potential and a second oxidation-reduction potential, and
the first active material has an equilibrium potential higher than the first oxidation-reduction potential and lower than the second oxidation-reduction potential.

10. The flow battery according to claim 1, wherein
the first circulation mechanism includes a first container,
the first container contains the first active material and the first liquid,
the first circulation mechanism circulates the first liquid between the first electrode and the first container, and
contact between the first active material and the first liquid in the first container causes at least one of an oxidation reaction and a reduction reaction between the first active material and the first electrode mediator.

11. The flow battery according to claim 10, wherein
the first circulation mechanism includes a first transfer prevention unit that prevents transfer of the first active material, and
the first transfer prevention unit is disposed on a path through which the first liquid flows from the first container to the first electrode.

12. The flow battery according to claim 1, further comprising:
a second liquid containing a charge mediator and a discharge mediator dissolved therein;
a second electrode immersed in the second liquid;
a second active material immersed in the second liquid; and
a separating unit that separates the first electrode and the first liquid from the second electrode and the second liquid,
wherein the charge mediator has a lower equilibrium potential than the second active material, and
the discharge mediator has a higher equilibrium potential than the second active material.

13. The flow battery according to claim 12, wherein
the second liquid contains lithium dissolved therein,
the second active material adsorbs and desorbs the lithium,
when charging, the charge mediator is reduced on the second electrode, the charge mediator reduced on the second electrode is oxidized by the second active material, and the second active material adsorbs the lithium, and
when discharging, the second active material on which the lithium is adsorbed reduces the discharge mediator, the second active material desorbs the lithium, and the discharge mediator reduced by the second active material is oxidized on the second electrode.

14. The flow battery according to claim 13, wherein
when the charging, the discharge mediator is reduced on the second electrode, and
when the discharging, the charge mediator is oxidized on the second electrode.

15. The flow battery according to claim 12, wherein
the charge mediator and the discharge mediator are condensed aromatic compounds, and
the second liquid containing the condensed aromatic compounds dissolved therein causes a solvated electron of lithium to be released and thereby dissolves the lithium as a cation.

16. The flow battery according to claim 15, wherein the charge mediator is at least one selected from the group consisting of phenanthrene, biphenyl, O-terphenyl, triphenylene, and anthracene.

17. The flow battery according to claim 15, wherein the discharge mediator is at least one selected from the group consisting of phenanthroline, 2,2'-bipyridyl, benzophenone, trans-stilbene, 4,4'-bipyridyl, 3,3'-bipyridyl, 2,4'-bipyridyl, 2,3'-bipyridyl, cis-stilbene, acetophenone, propiophenone, butyrophenone, valerophenone, and ethylenediamine.

18. The flow battery according to claim 12, further comprising:
a second circulation mechanism including a second container,
wherein the second active material and the second liquid are contained in the second container,
the second circulation mechanism circulates the second liquid between the second electrode and the second container, and
contact between the second active material and the second liquid in the second container causes at least one of an oxidation reaction of the charge mediator with the second active material and a reduction reaction of the discharge mediator with the second active material.

19. The flow battery according to claim 18, wherein
the second circulation mechanism includes a second transfer prevention unit that prevents transfer of the second active material, and
the second transfer prevention unit is disposed on a path through which the second liquid flows from the second container to the second electrode.

* * * * *